US010597351B2

(12) United States Patent
Restelli et al.

(10) Patent No.: US 10,597,351 B2
(45) Date of Patent: Mar. 24, 2020

(54) METHOD FOR PREPARING SELEGILINE BASE

(71) Applicant: Dipharma Francis S.r.l., Baranzate (MI) (IT)

(72) Inventors: Alessandro Restelli, Baranzate (IT); Gabriele Razzetti, Baranzate (IT); Alessandro de Marco, Baranzate (IT)

(73) Assignee: Dipharma Francis S.r.L., Baranzate (MI) (IT)

( * ) Notice: Subject to any disclaimer, the term of this patent is extended or adjusted under 35 U.S.C. 154(b) by 0 days.

(21) Appl. No.: 15/878,877

(22) Filed: Jan. 24, 2018

(65) Prior Publication Data

US 2018/0208542 A1 Jul. 26, 2018

(30) Foreign Application Priority Data

Jan. 26, 2017 (IT) ......................... 102017000008702

(51) Int. Cl.
*C07C 209/68* (2006.01)
*A61P 25/16* (2006.01)
*A61K 31/137* (2006.01)
*C07C 211/27* (2006.01)
*C07C 209/08* (2006.01)
*C07C 209/84* (2006.01)

(52) U.S. Cl.
CPC .......... *C07C 209/68* (2013.01); *A61K 31/137* (2013.01); *A61P 25/16* (2018.01); *C07C 209/08* (2013.01); *C07C 209/84* (2013.01); *C07C 211/27* (2013.01); *C07B 2200/07* (2013.01)

(58) Field of Classification Search
CPC ... C07C 209/08; C07C 209/68; C07C 209/84; C07C 211/27; C07B 2200/07
See application file for complete search history.

(56) References Cited

U.S. PATENT DOCUMENTS 3,496,195 A * 2/1970 Ecsery ................ C07D 307/33
534/558
2011/0184071 A1* 7/2011 Gore ...................... C07C 209/08
514/657

FOREIGN PATENT DOCUMENTS

EP 0099302 B1 10/1986
EP 0344675 B1 8/1993
GB 1031425 6/1966

OTHER PUBLICATIONS

Danafar "Simple and sensitive high performance liquid chromatographic (HPLC) method for the determination of the selegiline in human plasma" Cogent Medicine, 2016, 3, 1179244: https://www.cogentoa.com/article/10.1080/2331205X.2016.1179244 (Year: 2016).*
Le Droumaguet et al., "Selegiline-functionalized, PEGylated poly(alkyl cyanoacrylate) nanoparticles: Investigation of interaction with amyloid-β peptide and surface reorganization", International Journal of Pharmaceutics, 416 (2011) 453-460.

* cited by examiner

*Primary Examiner* — Amy C Bonaparte
(74) *Attorney, Agent, or Firm* — Rothwell, Figg, Ernst & Manback, P.C.

(57) ABSTRACT

The present invention relates to a process for the preparation of selegiline base, an irreversible and selective inhibitor of the MAO-B enzymes and which is used in the treatment of Parkinson's Disease.

14 Claims, 1 Drawing Sheet

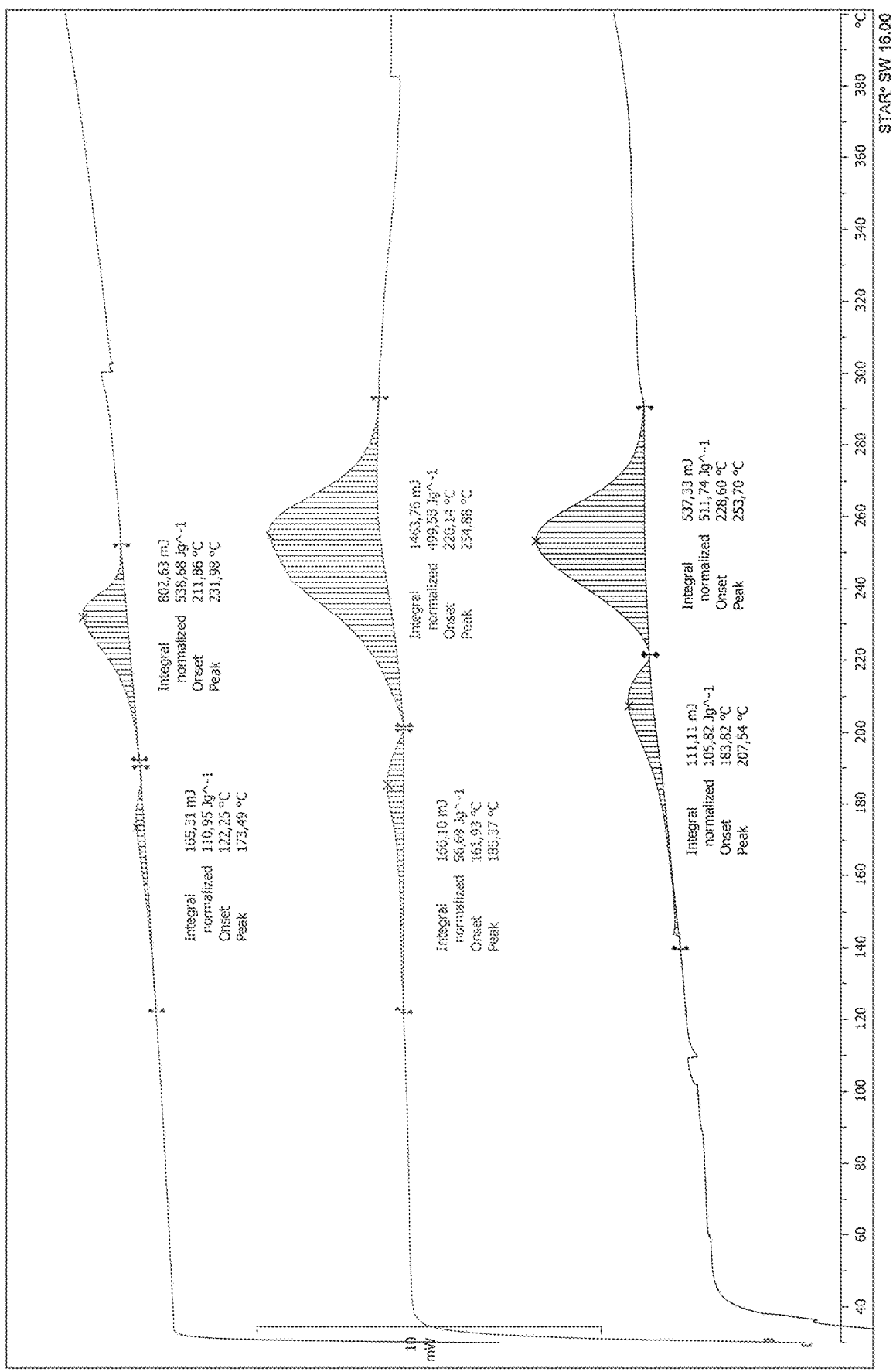

METHOD FOR PREPARING SELEGILINE BASE

FIELD OF THE INVENTION

The present invention relates to a process for the preparation of selegiline base, an irreversible and selective inhibitor of the MAO-B enzymes and which is used in the treatment of Parkinson's Disease.

PRIOR ART

The present invention relates to a novel process for the preparation and the industrial production of selegiline base, i.e. methyl-(1-methyl-2-phenyl-ethyl)-prop-2-ynyl-amine or N-α-dimethyl-N-2-propynyl-benzeneethanamine, of formula (I):

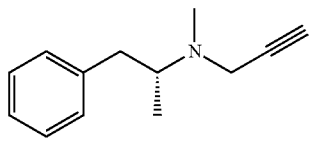

(I)

Selegiline base of formula (I) and its hydrochloride salt of formula (II) are known substances, in particular in the form of the (R)-(−)-enantiomers as selective inhibitors of monoamine oxidase B (MAO-B) and are used in the treatment of Parkinson's Disease.

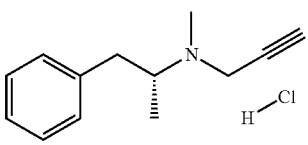

(II)

Several processes for the preparation of selegiline base are described in the literature, including the reaction between levomethamphetamine of formula (III),

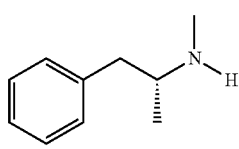

(III)

with propargyl bromide of formula (IV),

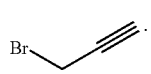

(IV)

The reaction can be carried out at high temperatures, such as for example at 100° C. as described in GB 1 031 425 or at 80° C. in toluene as described in U.S. Pat. No. 3,496,195, or at about 65° C. in a binary phase consisting of benzene and a sodium hydroxide aqueous solution, as known from EP 0 099 302.

The drawbacks of these procedures are related to the instability of some intermediates at high temperatures, for instance the polymerization of propargyl bromide at high temperatures, in particular in presence of strong bases.

The method disclosed by Le Droumaguet et al. in Int. J. Pharm. 2011, 416, 453-460 attempts to solve the above problem by purifying selegiline base comprising the reaction of the hydrochloride addition salt of selegiline of formula (II) with a $Na_2CO_3$ in aqueous solution. However, the procedure requires an extraction step using hazardous diethylether. In addition, the extraction solvent has to be removed by distillation.

A further method is disclosed in the patent application EP 0 344 675, wherein the inventors attempt to solve the above problem by performing the reaction between the levomethamphetamine of formula (III) with propargyl bromide of formula (IV) in the presence of anhydrous potassium carbonate at temperatures lower than 30/35° C. in a mixture water/chloroform, or at 5° C. in methanol. Then, the crude reaction mixture, which no longer contains the unstable compound of formula (IV), is purified by distillation and selegiline is isolated in the fraction, which evaporates between 126 to 129° C.

The inventors of the present invention have proved by DSC analysis that a degradation of the product occurs at the temperature of the distillation. The inventors of the present invention have measured that the decomposition energy of selegiline base is 790 J/g. After an incubation of the compound for 36 hours at 130° C. the decomposition energy drops almost by 10% to 722 J/g, which indicates a partial degradation of the product. The boiling temperature of selegiline can be lowered by reducing the pressure below 6 mbar. At that pressure the product can be distilled at 105-110° C. and this leads to a reduced amount of degraded product.

The inventors have further investigated by DSC analysis the crude reaction mixture of selegiline base, obtained by concentration to dryness of the solution of the reaction product of levomethamphetamine of formula (III) and propargyl bromide of formula (IV).

The analysis reveals two exothermic phenomena in sequence. The first begins at a temperature of about 160° C. and produces an energy of 100 J/g the second begins immediately after the end of the first event (220° C. approximately) and terminates at about 290° C. and develops an exothermic energy equal to about 525 J/g. The two phenomena are consecutive and the summary of the two decomposition heats exceeds 600 J/g as shown in FIG. 1.

It is generally advisable that the reaction and purification temperature should be below the temperatures, which trigger exothermic reactions, in order to minimize the risk of accidents. A rule of thumb that is widely followed is that the reaction (or purification) temperature should be at least 100° C. below the exothermic event (established by DSC) to prevent that the reaction or the purification may assume an explosive character (P. Cardillo, Accidents in the Chemical Environment, Stazione sperimentale per i Combustibili San Donato Milanese 1998).

The inventors of the present invention have found a new and safe alternative method for the preparation of selegiline base, which overcomes the above-mentioned problems. The new method provides selegiline base at high yields and thus it is particularly suitable for a production of the product at an industrial level.

BRIEF DESCRIPTION OF THE FIGURE AND OF ANALYTICAL METHODS

The DSC experiments were performed using a Mettler-Toledo DSC 822e differential scanning calorimeter with the following operating conditions: gold capsules, range from 30° C. to 400° C. at a scanning speed of 2-5-10° C./min (in specific, 2° C. for the first run, 5° C. for the second and 10° C. for the third one). No purge gas was used.

FIG. 1 shows the DSC trace of selegiline obtained by concentration to dryness of the reaction mixture between levomethamphetamine of formula (III) and propargyl bromide of formula (IV).

SUMMARY OF THE INVENTION

The object of the present invention is a process for the preparation of selegiline base, comprising the reaction of the solid hydrochloride salt of selegiline with a base in an aqueous solution, the separation of selegiline base from the aqueous solution and the drying of the product. This method allows to avoid the hazardous distillation procedure of selegiline base, which also causes a significant degradation of the product, and to obtain safely a product at a high purity, which meets the mandatory regulatory requirements for selegiline API.

DETAILED DESCRIPTION OF THE INVENTION

The invention provides, as the first object, a process for the preparation of selegiline base, having the following formula (I):

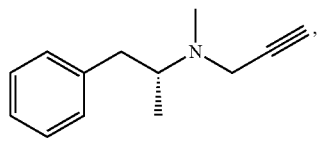

(I)

comprising:
the reaction of the hydrochloride addition salt of selegiline of formula (II)

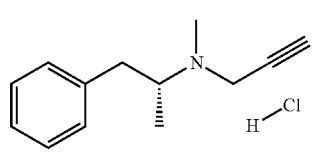

(II)

with a base in an aqueous solution forming a biphasic mixture;
the separation of selegiline base of formula (I) from the aqueous solution;
the anhydrification by drying selegiline base of formula (I) or by freezing selegiline base of formula (I) at temperatures below 0° C.
and wherein the ratio of the hydrochloride addition salt of selegiline of formula (II) and the aqueous content during the reaction of the hydrochloride addition salt with the base is equal or superior to 100 mg/1 mL water.

By "comprising" herein is meant that additional steps may be taken in the processing, which do not substantially change the product produced by the reaction. The term comprising encompasses the terms "consisting of" and "consisting essentially of".

The hydrochloride addition salt of selegiline of formula (II) is preferably in solid form.

A base suitable for the aqueous solution can be an inorganic base, typically an inorganic base selected from the group comprising a hydroxide or a carbonate or a bicarbonate of an alkali metal or an alkaline earth metal, for example lithium, sodium or potassium hydroxide, sodium bicarbonate, potassium bicarbonate, sodium carbonate or potassium carbonate. Preferably, the inorganic base is sodium hydroxide.

The treatment of the hydrochloride salt of selegiline of formula (II) with an inorganic base according to the present invention leads to a biphasic mixture, which can be optionally filtered on perlite. The aqueous phase is then discarded. The formation of the biphasic mixture and the subsequent simple separation of selegiline base of formula (I) without any extraction or distillation steps provides a key advantage over the prior art procedures. As stated already above, the product can be separated without any step that requires heating up, which not only may provide a product with a lower purity. This alternative method is also safer, in particular if performed at an industrial scale.

For obtaining said biphasic mixture and also to minimize the risk that any selegiline base of formula (I) remains in the aqueous phase, it is important that the ratio between the hydrochloride salt of selegiline of formula (II) and water is sufficiently high. For instance, the ratio is 100 mg of hydrochloride salt of selegiline of formula (II)/1 mL of water or higher, preferably 100 mg/0.5 mL or higher, more preferably about 100 mg of hydrochloride salt of selegiline of formula (II) in 0.1 mL of water. Examples of said ratio can be equal or superior to 100 mg/1 mL, 200 mg/1 mL, 300 mg/1 mL, 400 mg/1 mL, 500 mg/1 mL, 600 mg/1 mL, 700 mg/1 mL, 800 mg/1 mL, 900 mg/1 mL, 1000 mg/mL or higher.

The oily phase containing selegiline base of formula (I) can be dried by anhydrification or by freezing at temperatures below 0° C.

The anhydrification can be carried out by drying with a dehydrating agent such as sodium sulfate ($Na_2SO_4$), magnesium sulfate ($MgSO_4$), sodium carbonate ($Na_2CO_3$), potassium carbonate ($K_2CO_3$), sodium hydroxide (NaOH) or anhydrous calcium chloride ($CaCl_2$), preferably potassium carbonate ($K_2CO_3$).

According to the present invention, this process can be carried out at a temperature well below 100° C. and thus is a safe procedure, wherein no decomposition of selegiline base occurs. Preferably, the reaction can be carried out at a temperature between about 10° C. and 40° C., more preferably between about 20° C. and 30° C.

Moreover, according to the present invention, this process can be performed without any distillation step, neither of any solvent nor of selegiline base of formula (I).

In addition, according to the present invention, this process can be carried out without any organic solvent. According to the present invention, this process can be carried out solely using water as solvent.

Therefore, this procedure is particularly suitable for obtaining selegiline base of formula (I) of high purity and devoid of traces of organic solvents.

The hydrochloride salt of selegiline of formula (II) in solid form is a known compound. It can be obtained, for example, as described in EP 0 344 675 by reaction of hydrochloric acid (HCl) with selegiline crude base of formula (I) in a solvent, preferably in a $C_1$-$C_5$ alcohol, more preferably isopropanol, thus forming the hydrochloride of selegiline of formula (II) in solid form, preferably in crystalline form.

A $C_1$-$C_5$ alcohol can be linear or branched and it is preferably ethanol, 1-propanol, 2-propanol, 1-butanol, 2-butanol, tert-butanol, 1-pentanol, 2-pentanol or 3-pentanol.

Selegiline crude base of formula (I) is a known compound. It can be obtained for example by reaction of levomethamphetamine of formula (III):

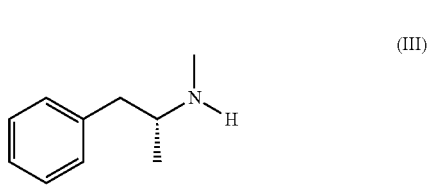

with propargyl bromide of formula (IV):

The reaction of levomethamphetamine of formula (III) with propargyl bromide of formula (IV) can be carried out neat, thus in the absence of any further solvent, as for example described in Example 5 of British patent application GB 1 031 425, or in the presence of a solvent, such as toluene as described in Example 1 of U.S. Pat. No. 3,496,195.

Both experimental procedures disclosed in GB 1 031 425 and in U.S. Pat. No. 3,496,195 describe that selegiline crude base obtained after the reaction is purified by distillation. The inventors of the present invention disclose herein a method for obtaining highly pure selegiline base API, wherein no purification by distillation has to be carried out. In fact, selegiline crude base obtained after the reaction by levomethamphetamine of formula (III) with propargyl bromide of formula (IV) can be directly converted into the hydrochloride of selegiline of formula (II).

Selegiline base of formula (I) obtained by the above method has a chemical purity, evaluated by HPLC at 225 nm, equal to or greater than 99.5% (Area %), preferably equal to or greater than 99.9%, more preferably equal to 100.0%, and wherein each impurity is present in a percentage equal to or lower than 0.2%, preferably equal to or less than 0.05% and wherein in the herein disclosed procedure none of the impurities increase by more than 0.03%, preferably none of the impurities increase by more than 0.01%.

The following example further illustrates the invention.

Example—Synthesis of Selegiline Base of Formula (I)

67 mL of NaOH 30% (% weight per weight (w/w)) and 50 mL of water are added to 100 g (0.447 moles) of selegiline hydrochloride. The solution is stirred for at least 30 minutes at a temperature between 20 and 30° C. Then, the biphasic mixture is filtered on perlite, the aqueous phase is discarded and 6.2 g of anhydrous potassium carbonate are added to the organic phase. If necessary, further potassium carbonate can be added. The oily product is separated to provide 79.0 g (molar yield of 94.4%) of selegiline base as an oil with a water content<0.5% (Karl-Fischer analysis) and a purity of 100% (HPLC detector at 225 nm). $^1$H-NMR (300 MHz, CDCl$_3$) δ: 7.40-7.20 (5H, m), 3.44 (2H, m), 3.00 (1H, m), 2.40 (5H, m), 2.25 (1H, m), 0.99 (3H, dd).

The invention claimed is:

1. A process for the preparation of selegiline base of formula (I):

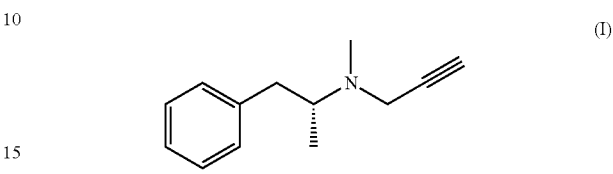

comprising:
a) reacting the hydrochloride addition salt of selegiline of formula (II)

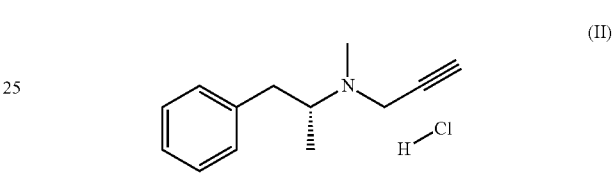

with a base in an aqueous solution forming a biphasic mixture;
b) separating any selegiline base of formula (I) from the aqueous solution; and
c) anhydrifying by drying the selegiline base of formula (I) or by freezing the selegiline base of formula (I) at a temperature below 0° C.,
wherein the ratio of the hydrochloride addition salt of selegiline of formula (II) and the aqueous content during step a) is equal or superior to 100 mg/1 mL water.

2. The process according to claim 1, wherein the hydrochloride addition salt of selegiline of formula (II) is in solid form and is reacted with the base in the aqueous solution.

3. The process according to claim 1, wherein the base is an inorganic base.

4. The process according to claim 3, wherein the inorganic base is an alkaline or alkaline earth metal hydroxide, carbonate or bicarbonate.

5. The process according to claim 3, wherein the inorganic base is lithium, sodium or potassium hydroxide or sodium bicarbonate, potassium bicarbonate, sodium carbonate or potassium carbonate.

6. The process according to claim 3, wherein the inorganic base is sodium hydroxide.

7. The process according to claim 1, wherein the reaction of the hydrochloride addition salt of selegiline of formula (II) with the base is carried out at a temperature between 10° C. to 40° C.

8. The process according to claim 1, wherein the reaction of the hydrochloride addition salt of selegiline of formula (II) with the base is carried out at a temperature between 20° C. to 30° C.

9. The process according to claim 1, wherein the drying of the selegiline base of formula (I) is carried out by anhydrification with a dehydrating agent selected from the group consisting of sodium sulfate (Na$_2$SO$_4$), magnesium sulfate (MgSO$_4$), sodium carbonate (Na$_2$CO$_3$), potassium carbonate (K$_2$CO$_3$), NaOH and anhydrous calcium chloride (CaCl$_2$).

10. The process according to claim 9, wherein the drying of selegiline base of formula (I) is carried out by anhydrification with potassium carbonate (K$_2$CO$_3$).

11. The process according to claim 1, wherein the hydrochloride addition salt of selegiline of formula (II) is added in a step a) in solid form and is obtained by a process comprising: reacting hydrochloric acid (HCl) with a selegiline crude base of formula (I) in a solvent; and obtaining the hydrochloride addition salt of selegiline of formula (II) in solid form.

12. The process according to claim 11, wherein the solvent is a C$_1$-C$_5$ alcohol.

13. The process according to claim 11, wherein the solvent is isopropanol.

14. The process according to claim 11, wherein the selegiline crude base of formula (I) is obtained by reaction of levo-methamphetamine of formula (III):

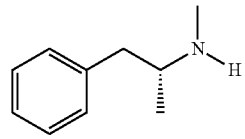

(III)

with propargyl bromide of formula (IV):

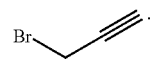

(IV)

* * * * *